(12) United States Patent
Inoue

(10) Patent No.: US 9,538,746 B2
(45) Date of Patent: *Jan. 10, 2017

(54) LIVING CELL CRYOPRESERVATION TOOL

(71) Applicant: Kitazato BioPharma Co., Ltd., Shizuoka (JP)

(72) Inventor: Futoshi Inoue, Fujinomiya (JP)

(73) Assignee: KITAZATO BIOPHARMA CO., LTD., Shizuoka (JP)

( * ) Notice: Subject to any disclaimer, the term of this patent is extended or adjusted under 35 U.S.C. 154(b) by 126 days.

This patent is subject to a terminal disclaimer.

(21) Appl. No.: 14/349,169

(22) PCT Filed: Oct. 1, 2012

(86) PCT No.: PCT/JP2012/075431
§ 371 (c)(1),
(2) Date: Apr. 2, 2014

(87) PCT Pub. No.: WO2013/051520
PCT Pub. Date: Apr. 11, 2013

(65) Prior Publication Data
US 2014/0212962 A1    Jul. 31, 2014

(30) Foreign Application Priority Data

Oct. 3, 2011 (JP) .................................. 2011-219592

(51) Int. Cl.
*A01N 1/02* (2006.01)
*C12M 1/00* (2006.01)
*A61B 17/435* (2006.01)

(52) U.S. Cl.
CPC ........... *A01N 1/0257* (2013.01); *A01N 1/0268* (2013.01); *C12M 45/22* (2013.01); *A61B 17/435* (2013.01)

(58) Field of Classification Search
CPC ..... C12M 45/22; A01N 1/0257; A01N 1/0268
See application file for complete search history.

(56) References Cited

U.S. PATENT DOCUMENTS

2004/0259072 A1    12/2004  Kuwayama et al.
2008/0038155 A1     2/2008  Chian et al.
(Continued)

FOREIGN PATENT DOCUMENTS

CN      101087658 A    12/2007
JP      2000-189155 A   7/2000
(Continued)

OTHER PUBLICATIONS

Notification of Transmittal of Translation of the International Preliminary Report on Patentability (Forms PCT/IB/338 and PCT/IB/373) and the Written Opinion of the International Searching Authority (Form PCT/ISA/237) issued on Apr. 17, 2014, by the International Bureau of WIPO in corresponding International Application No. PCT/JP2012/075431. (7 pages).

(Continued)

*Primary Examiner* — Gautam Prakash
(74) *Attorney, Agent, or Firm* — Buchanan Ingersoll & Rooney PC

(57) ABSTRACT

A living cell cryopreservation tool has a body part formed of a cold-resistant material and a living cell holding part formed of the cold-resistant material. The living cell holding part has a long and narrow living cell attaching and holding portion. The living cell attaching and holding portion has a plurality of living cell accommodation concave portions formed in a longitudinal direction thereof and a plurality of excess cryopreservation liquid discharge passages communicating with the living cell accommodation concave portions.

15 Claims, 10 Drawing Sheets

(56) References Cited

U.S. PATENT DOCUMENTS

| | | | |
|---|---|---|---|
| 2009/0123992 A1 | 5/2009 | Chin | |
| 2009/0298116 A1 | 12/2009 | Fang et al. | |
| 2010/0151570 A1* | 6/2010 | Kader et al. | A01N 1/02 |
| | | | 435/374 |
| 2010/0317108 A1* | 12/2010 | Stojanov | A01N 1/02 |
| | | | 435/374 |
| 2011/0129811 A1* | 6/2011 | Tao | A01N 1/0268 |
| | | | 435/1.3 |
| 2011/0196358 A1 | 8/2011 | Criado Scholz | |
| 2011/0207215 A1 | 8/2011 | Itchoda et al. | |
| 2011/0275153 A1* | 11/2011 | Butler et al. | A01N 1/0268 |
| | | | 435/374 |

FOREIGN PATENT DOCUMENTS

| | | |
|---|---|---|
| JP | 2002-315573 A | 10/2002 |
| JP | 2004-329202 A | 11/2004 |
| JP | 2010-148457 A | 7/2010 |
| WO | WO 02/085110 A1 | 10/2002 |
| WO | 2010/047133 A1 | 4/2010 |

OTHER PUBLICATIONS

U.S. Appl. No. 14/249,244, filed Apr. 2, 2014, Inoue.
U.S. Appl. No. 14/349,208, filed Apr. 2, 2014, Inoue.
Extended European Search Report dated May 28, 2015, issued by the European Patent Office in the corresponding European Application No. 12838223.1. (4 pages).
International Search Report (PCT/ISA/210) mailed on Jan. 8, 2013, by the Japanese Patent Office as the International Searching Authority for International Application No. PCT/JP2012/075431.

\* cited by examiner

US 9,538,746 B2

LIVING CELL CRYOPRESERVATION TOOL

TECHNICAL FIELD

The present invention relates to a cell cryopreservation tool to be used in cryopreservation living cells such as mammalian ova, eggs such as embryos, sperms, and stem cells such as hematopoietic stem cells, pluripotent stem cells, and the like.

BACKGROUND ART

Cryopreservation the mammalian embryo enables conservation of hereditary resources of specific systems and kinds. It is effective for maintaining animals standing on the brink of ruin. It is useful for infertility treatment.

As a method for cryopreservation mammalian embryos, as disclosed in a patent document 1 (Japanese Patent Application Laid-Open Publication No. 2000-189155), there is proposed a method for cryopreservation mammalian embryos that mammalian embryos or ova are bonded to the inner surface of the cryopreservation container such as the sterilized frozen straw, frozen vial or frozen tube by using a vitrifying liquid in an amount minimum and enough to enclose the mammalian embryos or the ova therewith. The cryopreservation container is sealed and rapidly cooled by bringing the cryopreservation container into contact with liquid nitrogen. In the thawing method, the cryopreservation container stored in the above method is taken out of the liquid nitrogen and one end thereof is opened. A diluted liquid of 33 to 39 degrees C. is injected directly into the container to thaw the mammalian embryos or the ova and dilute the vitrifying liquid. This method eliminates a possibility that the mammalian embryos or the ova are infected with a disease through viruses or bacteria and is capable of storing them at a high survival rate and thawing them and diluting the vitrifying liquid.

But the operation of bonding eggs such as embryos and ova to the inner surface of the cryopreservation container such as the frozen straw, the frozen vial or the frozen tube with the vitrifying liquid in an amount minimum and enough to enclose them therewith is not easy.

PRIOR ART DOCUMENTS

Patent Documents

Patent document 1: Japanese Patent Application Laid-Open Publication No. 2000-189155
Patent document 2: Japanese Patent Application Laid-Open Publication No. 2002-315573 (WO 02-085110 A1)
Patent document 3: Japanese Patent Application Laid-Open Publication No. 2004-329202 (US Patent Application Publication No. 2004-0259072)

SUMMARY OF THE INVENTION

Problems to be Solved by the Invention

The present applicant proposed an invention as disclosed in a patent document 2 (Japanese Patent Application Laid-Open Publication No. 2002-315573, WO 02-085110 A1). The egg cryopreservation tool 1 of the patent document 2 includes the body part 2 made of the cold-proof material; the egg attaching and holding strip 3, made of the material flexible, transparent, and resistant to liquid nitrogen, which is mounted at one end of the body part 2; and the cylindrical member 4, made of the cold-proof material and sealed at one end thereof, which allows the egg attaching and holding strip 3 to be enclosably and detachably mounted on the body part.

The present applicant also proposed an invention as disclosed in a patent document 3 (Japanese Patent Application Laid-Open Publication No. 2004-329202, US Patent Application Publication No. 2004-0259072). The egg cryopreservation tool 1 of the patent document 3 has the egg cryopreservation tube 2 formed of the liquid nitrogen-resistant material and the metal tubular protective member 3 for protecting the tube 2. The tube 2 has the body part 21 and the egg storing small-diameter part 22 having the inner diameter of 0.1 mm to 0.5 mm. The tube 2 can be heat-sealed at the front side of the small-diameter part and at the body part 21. The tubular protective member 3 has the tubular part 31 storing the front side of the small-diameter part 22 of the tube 2 and the semi-tubular part 32 storing the portion of the small-diameter part 22 not stored in the tubular part 31 and the front portion 21a of the body part 21. The egg cryopreservation tools of the patent documents 2 and 3 are effective.

But there is a demand for the development of a cryopreservation tool which allows an egg freezing operation to be easily performed and is capable of securely restraining frozen eggs to be separated from the egg cryopreservation tube 2.

Therefore it is an object of the present invention to provide a living cell cryopreservation tool which allows an operation of placing living cells thereon to be easily performed, prevents the living cells from separating therefrom while an operation of freezing the living cells is being performed, and allows the living cells to be quickly frozen.

Means for Solving the Problems

The means for achieving the above-described object is as described below.

A living cell cryopreservation tool of the present invention has a body part formed of a cold-resistant material and a living cell holding part formed of the cold-resistant material. The living cell holding part has a long and narrow living cell attaching and holding portion. The living cell attaching and holding portion has a plurality of living cell accommodation concave portions formed in a longitudinal direction thereof and a plurality of excess cryopreservation liquid discharge passages communicating with the living cell accommodation concave portions.

MODE FOR CARRYING OUT THE INVENTION

Figure 1:
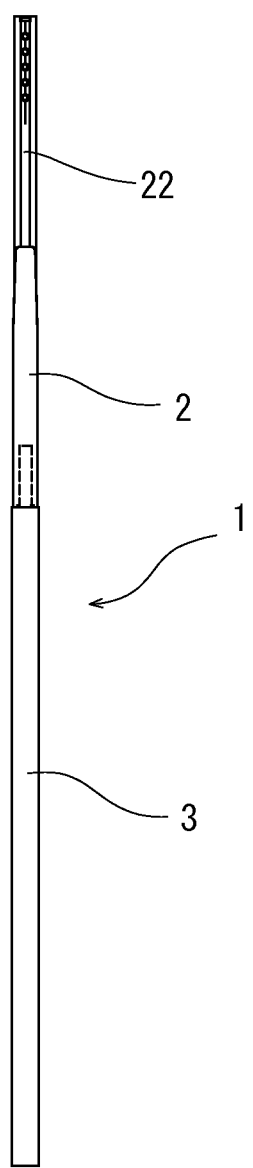
FIG. 1 is a front view of a living cell cryopreservation tool of an embodiment of the present invention.
Figure 2:
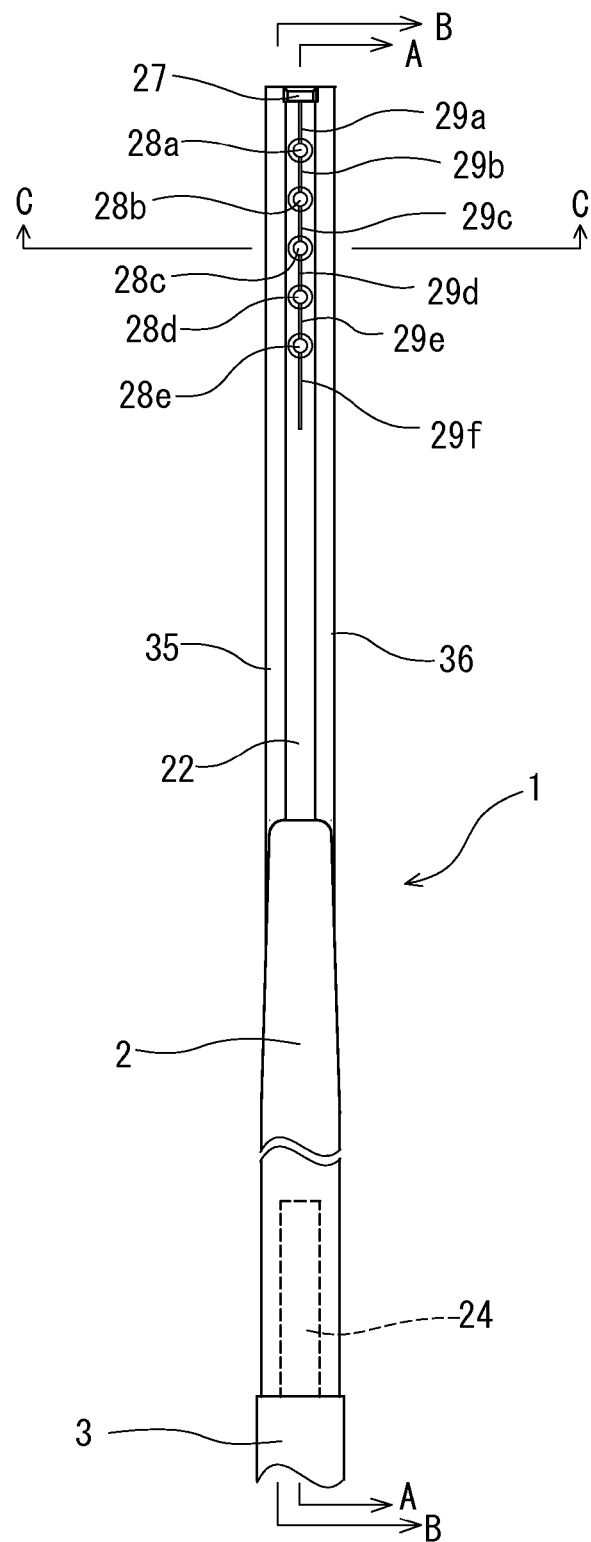
FIG. 2 is an enlarged front view of a distal portion of a living cell cryopreservation member shown in FIG. 1.
Figure 3:
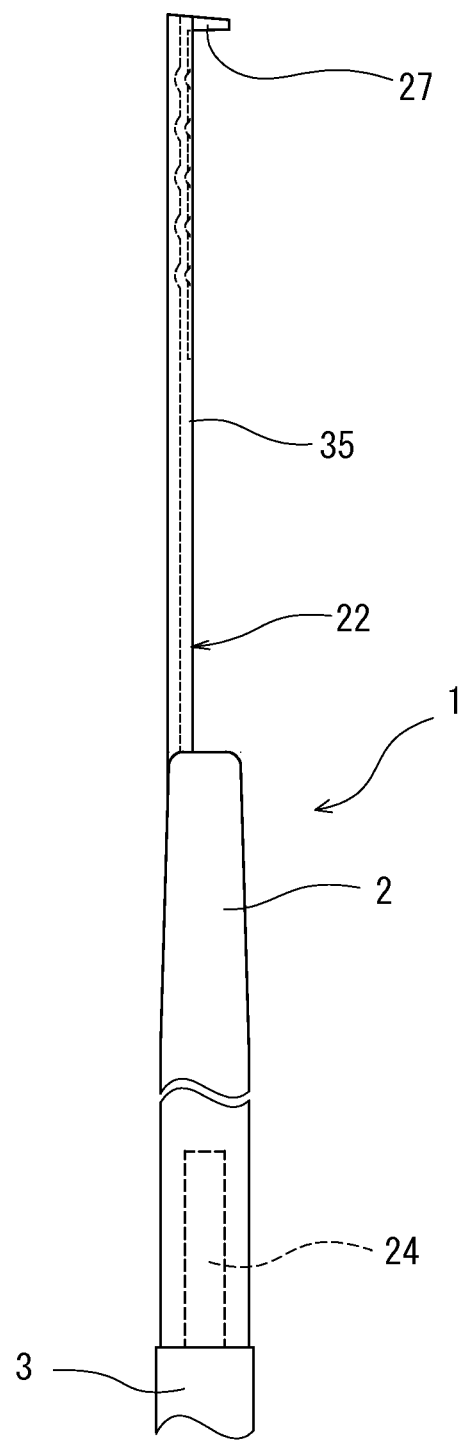
FIG. 3 is a left-side view of the living cell cryopreservation member shown in FIG. 2.

The living cell cryopreservation tool of the present invention will be described below by using embodiments shown in the drawings.

A living cell cryopreservation tool 1 of the present invention has a body part 3 formed of a cold-resistant material and a living cell holding part (egg holding part) 2 formed of the cold-resistant material. The egg holding part 2 has a long and narrow egg attaching and holding portion 22. The egg attaching and holding portion 22 has a plurality of living cell accommodation concave portions (egg accommodation concave portions) 28a, 28b, 28c, 28d, and 28e formed in a longitudinal direction of the egg attaching and holding portion 22 and a plurality of excess cryopreservation liquid discharge (exhaust) passages 29a, 29b, 29c, 29d, 29e, and 29f communicating with the living cell accommodation concave portions 28a, 28b, 28c, 28d, and 28e.

The cell cryopreservation tool 1 of this embodiment is an egg cryopreservation tool. The living cell holding part 2 is the egg holding part. The cell cryopreservation tool of the present invention can be used to freeze and store cells including eggs such as embryos, ova, sperms, and stem cells such as hematopoietic stem cells, pluripotent stem cells, and the like and particularly the above-described living cells.

As shown in FIGS. 1 through 5, the living cell cryopreservation tool 1 has the body part 3 formed of the cold-resistant material and the living cell holding part 2 formed of the cold-resistant material. In the living cell cryopreservation tool of this embodiment, as shown in FIGS. 2 through 5 (particularly FIG. 4), a hole portion 21a extended a predetermined length toward a distal end of the living cell holding part 2 is formed at a proximal portion thereof. A projected portion 24, extended a predetermined length, which is capable of penetrating into the hole portion 21a is formed at a distal portion of the body part 3. The projected portion 24 of the body part 3 is inserted into the hole portion 21a of the living cell holding part 2 to fix both portions 24 and 21a to each other.

The living cell holding part 2 has an approximately rectangular cross section. As described above, the living cell holding part 2 has the proximal portion connected with the body part 3 and the living cell attaching and holding portion 22 projected from the proximal portion thereof toward the distal end thereof. In the living cell cryopreservation tool of this embodiment, the living cell attaching and holding portion 22 has the shape of a long and narrow belt (thin plate-shaped). The surface of the living cell attaching and holding portion forms a living cell attaching and holding surface.

Figure 4:
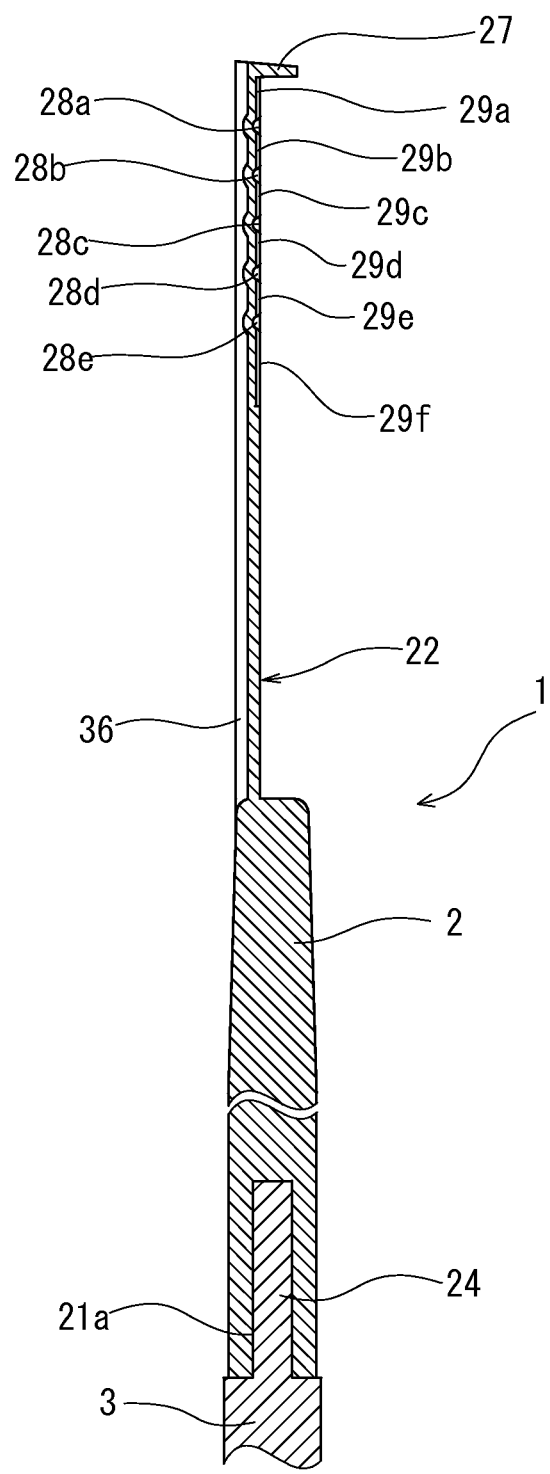
FIG. 4 is a sectional view taken along a line A-A of FIG. 2.
Figure 5:
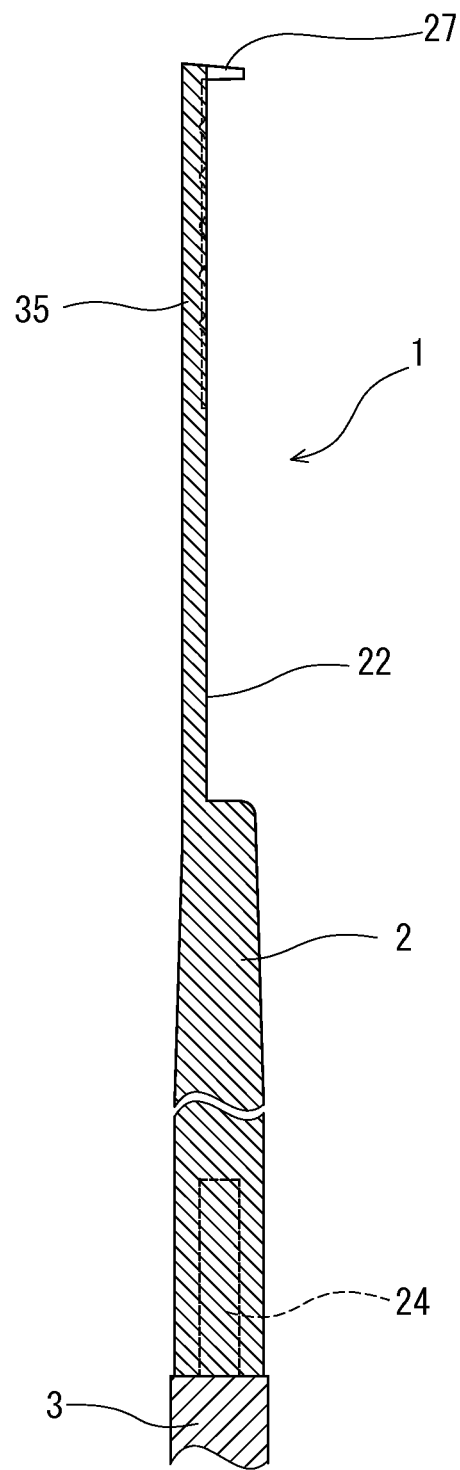
FIG. 5 is a sectional view taken along a line B-B of FIG. 2.
Figure 7:
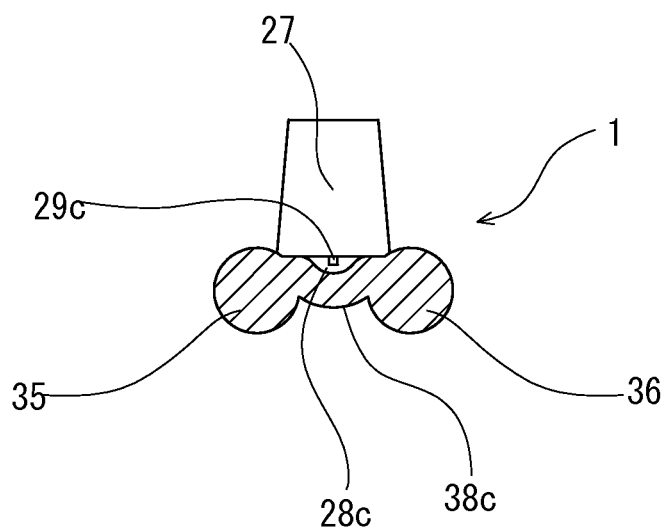
FIG. 7 is a sectional view taken along a line C-C of FIG. 2.
Figure 8:
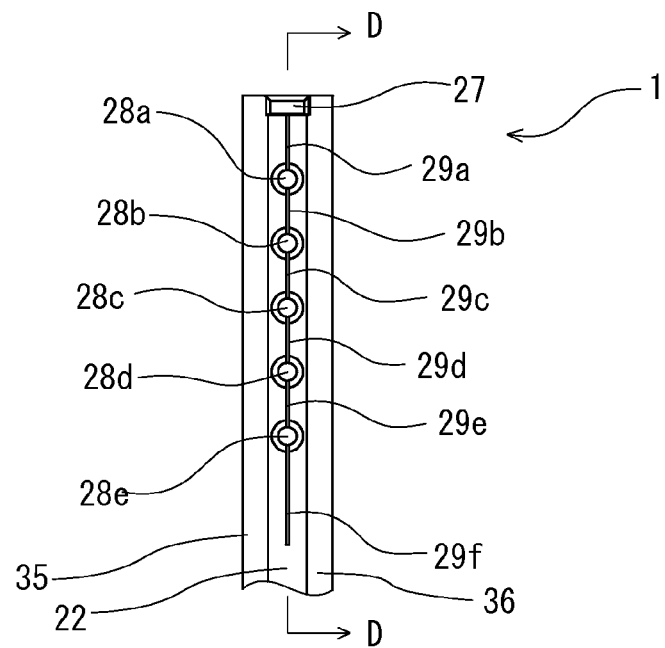
FIG. 8 is an enlarged front view of the distal portion of the living cell cryopreservation member shown in FIG. 1.
Figure 9:
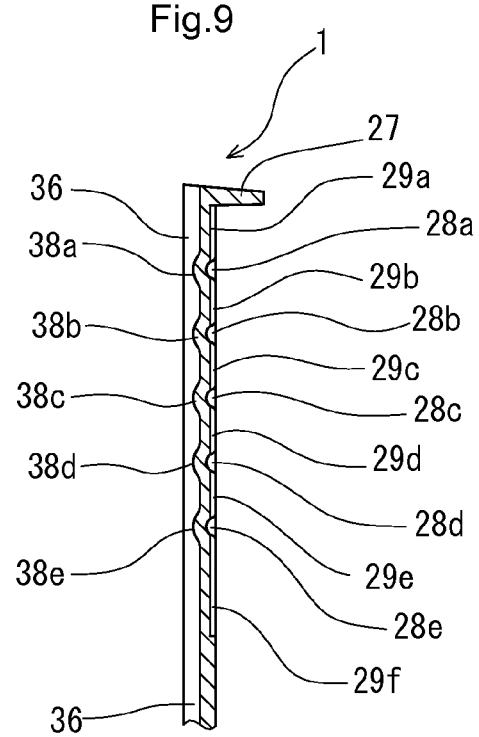
FIG. 9 is a sectional view taken along a line D-D of FIG. 8.

As shown in FIGS. 2 through 9, in the living cell cryopreservation tool 1 of the present invention, a plurality of the living cell accommodation concave portions 28a, 28b, 28c, 28d, and 28e is formed on the surface of the living cell attaching and holding portion 22 in its longitudinal direction. As shown in FIGS. 4 and 9, each of the living cell accommodation concave portions 28a, 28b, 28c, 28d, and 28e is formed as an approximately hemispherical concave portion. A plurality of the concave portions 28a, 28b, 28c, 28d, and 28e is linearly arranged on the living cell attaching and holding portion 22 from a position spaced at a predetermined interval from the distal end of the living cell cryopreservation tool 1 toward the proximal side thereof. The concave portions are spaced at almost regular intervals. Although a plurality of the concave portions is formed in this embodiment, the formation of one concave portion is allowed. In the case where a plurality of the concave portions is formed, it is preferable to form two to eight concave portions. It is preferable to set the depth of each concave portion to 0.05 to 0.5 mm and the diameter of an opening to be formed on the upper surface thereof to 0.1 to 0.5 mm. It is also preferable to set the spaced interval between the adjacent concave portions to 1 to 3 mm.

In the living cell cryopreservation tool of this embodiment, as shown in FIGS. 7 and 9, bulged portions 38a, 38b, 38c, 38d, and 38e are formed on a backside of each of the portions of the living cell attaching and holding portion 22 where the living cell accommodation concave portions 28a, 28b, 28c, 28d, and 28e are formed. Thus the portions thereof where the living cell accommodation concave portions are formed are not thin, but have a sufficient strength. The surface of the living cell cryopreservation tool 1 may be formed as a flat surface without forming the living cell accommodation concave portions to use the formed flat surface thereof as the living cell attaching and holding portion. It is preferable to set the width of the living cell attaching and holding portion 22 to 0.4 to 1.0 mm, its length to 5 to 30 mm, and its entire thickness and the thickness at the concave portions to 0.08 to 1.0 mm. It is preferable to set the length of the thick proximal portion of the living cell holding part 2 to 5 to 30 mm and the length of the body part to 20 to 100 mm.

Figure 6:
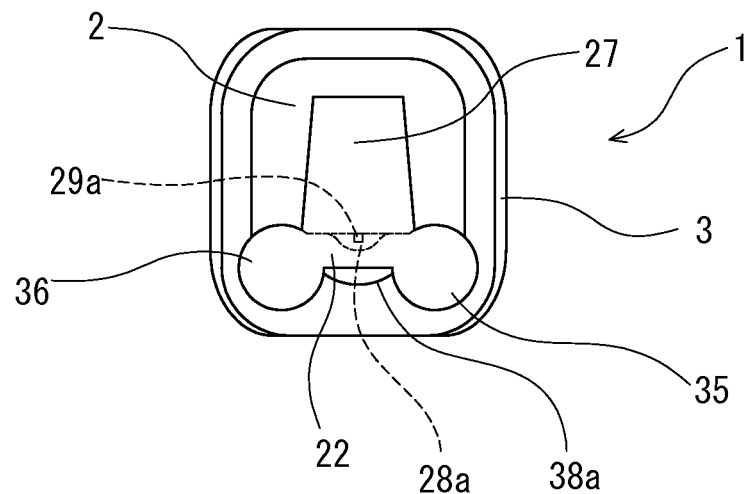
FIG. 6 is an enlarged plan view of the living cell cryopreservation member shown in FIG. 2.

As shown in FIGS. 6 through 8, the living cell cryopreservation tool 1 of this embodiment has two side bulged portions 35, 36, one of which is formed at one side of the portion of the living cell attaching and holding portion 22 where the living cell accommodation concave portions 28a, 28b, 28c, 28d, and 28e are formed and the other of which is formed at the other side of the above-described portion. The two side bulged portions are extended in the longitudinal direction of the living cell attaching and holding portion 22. Because the living cell cryopreservation tool 1 has the bulged portion at both sides of the portion of the living cell attaching and holding portion where the living cell accommodation concave portions are formed, it is possible to securely restrain the living cells from moving to the sides of the living cell accommodation concave portions when the living cells are placed thereon and in addition prevent the living cells from separating therefrom.

As shown in FIGS. 1 through 9 (particularly FIGS. 6 and 7), in the living cell cryopreservation tool 1 of this embodiment, the living cell attaching and holding portion 22 has a projected portion 27 formed at a distal end side thereof than the living cell accommodation concave portions 28a, 28b, 28c, 28d, and 28e. The projected portion 27 is formed from the distal end of the living cell attaching and holding portion 22 toward an upper surface side (the side at which the living cell accommodation concave portions are formed) thereof. As shown in FIG. 9, the distal end surface of the projected portion 27 is formed as an inclined surface inclining a little toward the proximal side of the living cell attaching and holding portion. By forming the projected portion 27 having the above-described construction, it is possible to prevent the living cells from falling from the living cell cryopreservation tool 1, in other words, from the living cell attaching and holding portion 22, if the living cells separate from the living cell accommodation portion and move toward the distal side of the living cell attaching and holding portion. In the living cell cryopreservation tool 1 of this embodiment, as described above, in cooperation between the projected portion 27 and the side bulged portions 35, 36, one of which is formed at one side of the living cell attaching and holding portion 22 and the other of which is formed at the other side thereof, the living cells are prevented from falling from the living cell attaching and holding portion.

As shown in FIGS. 2 through 9 (particularly FIGS. 8 and 9), in the living cell cryopreservation tool 1 of this embodiment, the living cell attaching and holding portion 22 has the excess cryopreservation liquid discharge passages communicating with the living cell accommodation concave portions 28a, 28b, 28c, 28d, and 28e. In the living cell cryopreservation tool 1 of this embodiment, the excess cryopreservation liquid discharge passages are constructed of groove portions 29a, 29b, 29c, 29d, 29e, and 29f extended in the longitudinal direction of the living cell attaching and holding portion 22. In the living cell cryopreservation tool of this embodiment, each of the groove portions 29a, 29b, 29c, 29d, 29e, and 29f communicates the adjacent living cell accommodation concave portions to each other. More specifically, the groove portion 29b communicates the concave portions 28a and 28b to each other. The groove portion 29c communicates the concave portions 28b and 28c to each other. The groove portion 29d communicates the concave portions 28c and 28d to each other. The groove portion 29e communicates the concave portions 28d and 28e to each other.

As shown in FIGS. 8 and 9, in this embodiment, the living cell attaching and holding portion 22 has the groove portion 29a extended toward the distal end thereof from the living cell accommodation concave portion 28a positioned nearer to the distal end thereof than any other living cell accommodation concave portions. The distal end of the groove portion 29a reaches the above-described projected portion or is extended to the vicinity thereof. In the living cell cryopreservation tool of this embodiment, the living cell attaching and holding portion 22 has the groove portion 29f extended toward the proximal end thereof from the living cell accommodation concave portion 28e positioned nearer to the proximal end thereof than any other living cell accommodation concave portions.

By forming the excess cryopreservation liquid discharge passages, having the above-described construction, which communicate with the living cell accommodation concave portions, an excess amount of a cryopreservation liquid accommodated in the living cell accommodation concave portions together with the living cells flows into the groove portions. Thereby it is possible to prevent the living cells from being coated with the excess amount of the cryopreservation liquid and rapidly freeze the living cells. In addition, because the adjacent living cell accommodation concave portions communicate with each other through the groove portion, the cryopreservation liquid is capable of moving easily from the living cell accommodation concave portions to the grooves. Further an equal amount of the cryopreservation liquid remains in a plurality of the living cell accommodation concave portions. It is preferable to set the width of each groove portion to 100 µm to 500 µm and the depth thereof to 50 µm to 500 µm.

The body part 3 and the living cell holding part 2 are formed of the cold-resistant material. It is especially preferable to form the body part 3 and the living cell holding part 2 of a liquid nitrogen-resistant material. In other words, it is preferable to form them of a material which does not brittle when the material contacts liquid nitrogen. It is also preferable that the living cell holding part 2 is transparent or semitransparent and in addition flexible to some extent. As materials which form the body part 3 and the living cell holding part 2, synthetic resins such as 3-polyethylene fluoride, low-density polyethylene, medium-density polyethylene, high-density polyethylene, polycarbonate, nylon, polysulfone, polyester, polystyrene, polyimide, ultra-high-molecular-weight polyethylene, ethylene-vinyl acetate copolymer; and laminates of films formed of these synthetic resins are preferably used.

As shown in FIGS. 6, 7, and 9 (particularly FIG. 7), in the living cell cryopreservation tool 1 of the above-described embodiment, the groove portions and the living cell accommodation concave portions are so constructed that the groove portions 29a, 29b, 29c, 29d, and 29e do not reach bottom portions of the living cell accommodation concave portions 28a, 28b, 28c, 28d, and 28e respectively. This construction allows a small amount of the cryopreservation liquid to be stored at the bottom portions of the living cell accommodation concave portions 28a, 28b, 28c, 28d, and 28e.

Figure 10:
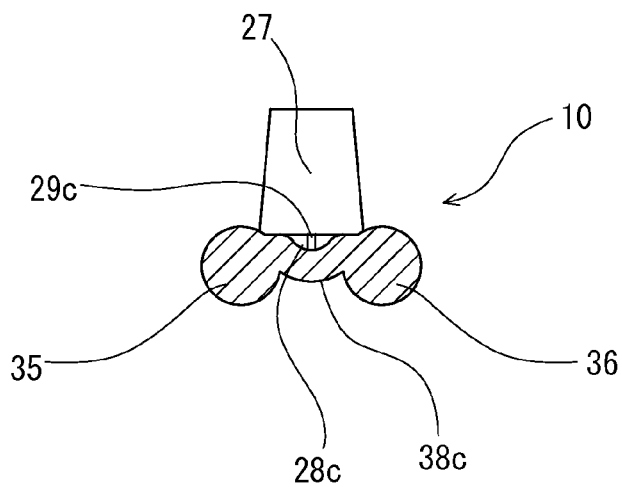
FIG. 10 is an enlarged cross-sectional view obtained by cutting a living cell cryopreservation member of another embodiment of the present invention at a living cell accommodation concave portion thereof.
Figure 11:
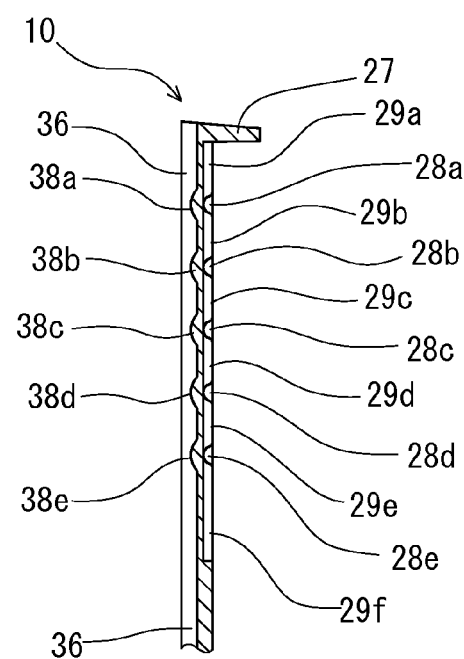
FIG. 11 is an enlarged longitudinal sectional view of a living cell cryopreservation member of another embodiment of the present invention.

The mode of the groove portions and that of the living cell accommodation concave portions are not limited to the above-described ones, but like a living cell cryopreservation tool 10 shown in FIGS. 10 and 11, the groove portions 29a, 29b, 29c, 29d, and 29e may reach the bottom portions of the living cell accommodation concave portions 28a, 28b, 28c, 28d, and 28e respectively. This construction allows a smaller amount of the cryopreservation liquid to be stored in the living cell accommodation concave portions 28a, 28b, 28c, 28d, and 28e.

The mode of the living cell accommodation concave portion and that of the excess cryopreservation liquid discharge passage communicating therewith are not limited to the above-described ones.

Figure 12:
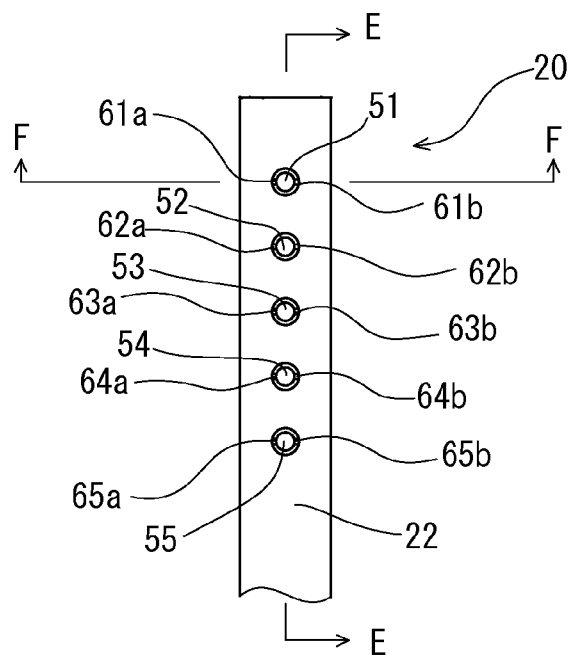
FIG. 12 is an enlarged front view of a distal portion of a living cell cryopreservation tool of another embodiment of the present invention.
Figure 13:
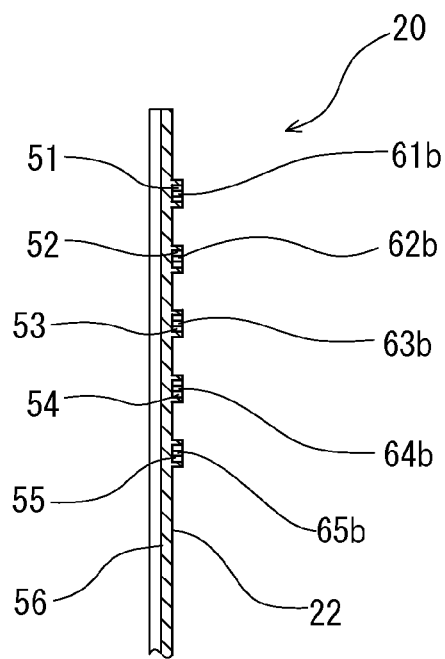
FIG. 13 is a sectional view taken along a line E-E of FIG. 12.
Figure 14:
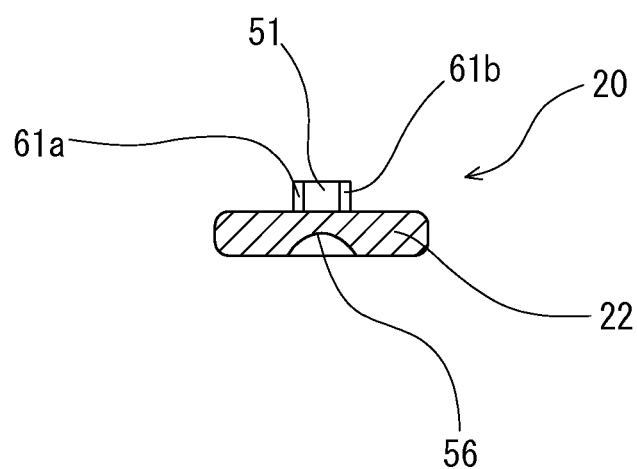
FIG. 14 is a sectional view taken along a line F-F of FIG. 12.

For example, a living cell cryopreservation tool 20 of a type as shown in FIGS. 12 through 14 may be adopted as the living cell cryopreservation tool of the present invention. FIG. 12 is an enlarged front view of a distal portion of a living cell cryopreservation tool of another embodiment of the present invention. FIG. 13 is a sectional view taken along a line E-E of FIG. 12. FIG. 14 is a sectional view taken along a line F-F of FIG. 12.

In the living cell cryopreservation tool 20, the living cell attaching and holding portion 22 has a plurality of short cylindrical projected portions formed on an upper surface thereof. Living cell accommodation concave portions 51, 52, 53, 54, and 55 are formed inside the projected portions respectively. There are formed on side walls of the projected portions two slits 61a, 61b communicating with the concave portion 51, two slits 62a, 62b communicating with the concave portion 52, two slits 63a, 63b communicating with the concave portion 53, two slits 64a, 64b communicating with the concave portion 54, and two slits 65a, 65b communicating with the concave portion 55. Each slit communicates with a bottom portion of the corresponding concave portion. The number of the slits which communicate with the corresponding concave portion may be one, but it is preferable to form not less than two slits. It is preferable to set the depth of the concave portion to 0.05 to 0.5 mm. The living cell cryopreservation tool 20 has a concave portion 56 formed at a backside thereof (side at which short cylindrical projected portions are not formed). The concave portion 56 axially extends and passes below the bottom surface of the concave portion 51. Thereby a portion forming the bottom surface of the concave portion 51 is thin, which allows heat conduction to the concave portion to be preferable.

The method of using the living cell cryopreservation tool 1 of the present invention is described below.

In the description made below, a case in which living cells (specifically ova) are frozen and stored is exemplified.

Initially an operation of collecting a plurality of ova which are living cells and replacing intracellular fluids of ova with equilibrium solutions is performed. Thereafter an operation of replacing the extracellular fluids with vitrifying liquids is performed. After ova are disposed together with a small amount of the vitrifying liquid at each of the living cell accommodation concave portions 28a, 28b, 28c, 28d, and 28e formed on the living cell attaching and holding portion 22 of the living cell cryopreservation tool 1 under a microscope, the ova are attached to the living cell accommodation concave portions. The living cell cryopreservation tool 1 to which the ova have attached is immersed in liquid nitrogen prepared in advance to freeze (vitrify) the ova. Owing to the contact between the liquid nitrogen and the living cells, the living cells are rapidly cooled. After the living cell cryopreservation tool 1 to which the frozen living cells have attached is accommodated in a tubular container separately prepared, the tubular container is accommodated in an accommodation container (cane). Thereafter the accommodation container is put in a liquid nitrogen tank to store the frozen living cells.

INDUSTRIAL APPLICABILITY

The living cell cryopreservation tool of the present invention is constructed as described below.

(1) A living cell cryopreservation tool comprising: a body part formed of a cold-resistant material and a living cell holding part formed of said cold-resistant material, wherein said living cell holding part has a long and narrow living cell attaching and holding portion; and said living cell attaching and holding portion has a plurality of living cell accommodation concave portions formed in a longitudinal direction thereof and excess cryopreservation liquid discharge passages communicating with said living cell accommodation concave portions.

In the living cell cryopreservation tool, owing to the formation of a plurality of the living cell accommodation concave portions at the living cell attaching and holding part, an operator can successfully dispose the living cells at the living cell attaching and holding part. Further because the living cells accommodated at the living cell accommodation concave portions are prevented from moving, it is possible to prevent the living cells from moving and separating therefrom in performing a freezing operation to be performed later. Furthermore because the living cell attaching and holding part has the excess cryopreservation liquid exhaust passages communicating with the living cell accommodation concave portions, the living cells can be quickly cooled in the freezing operation without stagnation of an excessive amount of the cryopreservation liquid at the living cell accommodation concave portions.

The embodiments of the present invention may be carried out as described below.

(2) A living cell cryopreservation tool according to the above (1), wherein said excess cryopreservation liquid discharge passages are constructed of groove portions which communicate with said living cell accommodation concave portions and are extended in a longitudinal direction of said living cell attaching and holding portion.

(3) A living cell cryopreservation tool according to the above (1) or (2), wherein said living cell holding part has two side bulged portions which are formed at both sides of a portion of said living cell attaching and holding portion where said living cell accommodation concave portions are formed and are extended in said longitudinal direction of said living cell attaching and holding portion.

(4) A living cell cryopreservation tool according to any one of the above (1) through (3), wherein said living cell attaching and holding portion has a projected portion formed at a position thereof nearer to a distal end thereof than said living cell accommodation concave portion positioned nearer to said distal end thereof than said other living cell accommodation concave portions.

(5) A living cell cryopreservation tool according to any one of the above (2) through (4), wherein each of said groove portions communicates said adjacent living cell accommodation concave portions to each other.

(6) A living cell cryopreservation tool according to any one of the above (2) through (5), wherein said living cell attaching and holding portion has a groove portion extended toward a distal end thereof from said living cell accommodation concave portion positioned nearer to said distal end thereof than any other living cell accommodation concave portions.

(7) A living cell cryopreservation tool according to any one of the above (2) through (6), wherein said living cell attaching and holding portion has a groove portion extended toward a proximal end thereof from said living cell accommodation concave portion positioned nearer to said proximal end thereof than any other living cell accommodation concave portions.

(8) A living cell cryopreservation tool according to any one of the above (1) through (7), wherein said cold-resistant material is a liquid nitrogen-resistant material.

(9) A living cell cryopreservation tool according to any one of the above (1) through (8), wherein said living cell attaching and holding portion is thin plate-shaped.

The invention claimed is:
1. A living cell cryopreservation tool comprising:
a body part and a living cell holding part projecting from said body part toward the distal side of said living cell holding part;
said body part is formed of a liquid nitrogen-resistant synthetic resin;
said living cell holding part is formed of a liquid nitrogen-resistant synthetic resin;
said living cell holding part is plate-shaped and extends in a longitudinal direction of said living cell cryopreservation tool;
said living cell holding part has a plurality of living cell accommodation concaves provided on a surface of said plate-shaped living cell holding part;
said plurality of living cell accommodation concaves are arranged in said longitudinal direction of said living cell cryopreservation tool;
said living cell accommodation concaves are approximately hemispherical concaves;

said living cell holding part has a groove communicating with said living cell accommodation concave and said living cell accommodation concave adjacent to each other; and said groove has cryopreservation liquid discharge passages in said living cell accommodation concave.

2. The cell cryopreservation tool according to claim 1, wherein said living cell holding part is transparent or semitransparent.

3. The cell cryopreservation tool according to claim 1, wherein said plurality of living cell accommodation concaves is linearly arranged on said living cell attaching and holding portion from a position spaced at a predetermined interval from a distal end of said cryopreservation tool toward a proximal side thereof.

4. The living cell cryopreservation tool according to claim 1, wherein said living cell attaching and holding portion has bulged portions formed on a backside of each of the portions of said living cell attaching and holding portion.

5. The living cell cryopreservation tool according to claim 1, wherein said living cell holding part has two side bulged portions which are formed at both sides of a portion of said living cell attaching and holding portion where said living cell accommodation concaves are formed and are extended in said longitudinal direction of said living cell attaching and holding portion.

6. The living cell cryopreservation tool according to claim 1, wherein said living cell attaching and holding portion has a projected portion formed at a distal end side thereof than said living cell accommodation concave positioned nearer to said distal end thereof than said other living cell accommodation concaves.

7. The living cell cryopreservation tool according to claim 1, wherein said living cell attaching and holding portion has a distal groove extended toward a distal end thereof from said living cell accommodation concave positioned nearer to said distal end thereof than any other living cell accommodation concaves.

8. The living cell cryopreservation tool according to claim 1, wherein said living cell attaching and holding portion has a distal groove extending toward a distal end thereof from said living cell accommodation concave positioned nearer to said distal end thereof than any other living cell accommodation concaves and a projected portion formed at a distal end side thereof than said living cell accommodation concave positioned nearer to said distal end thereof than said other living cell accommodation concaves.

9. The living cell cryopreservation tool according to claim 1, wherein said living cell attaching and holding portion has a proximal groove extended toward a proximal end thereof from said living cell accommodation concave portion positioned nearer to said proximal end thereof than any other living cell accommodation concaves.

10. A living cell cryopreservation tool comprising:
a body part and a living cell holding part projecting from said body part toward the distal side of said living cell holding part; and
wherein said body part is formed of a liquid nitrogen-resistant synthetic resin;
said living cell holding part is formed of a liquid nitrogen-resistant synthetic resin;
said living cell holding part is plate-shaped and extends in a longitudinal direction of said living cell cryopreservation tool;
said living cell holding part has a plurality of living cell accommodation concaves provided on a surface of said plate-shaped living cell holding part;

said plurality of living cell accommodation concaves are arranged in said longitudinal direction of said living cell cryopreservation tool;
said living cell accommodation concaves are approximately hemispherical concave portions;
said living cell holding part having a groove communicating with said living cell accommodation concave and said living cell accommodation concave adjacent to each other;
said living cell holding part having a distal groove extended toward a distal end thereof from said living cell accommodation concave positioned to a distal side than any other living cell accommodation concaves;
said living cell holding part having a proximal groove extended toward a proximal end thereof from said living cell accommodation concave positioned to a proximal side than any other living cell accommodation concaves; and
wherein said grooves having cryopreservation liquid discharge passages in said living cell accommodation concave.

11. The living cell cryopreservation tool according to claim 10, wherein said living cell holding part has two side bulged portions which are formed at both sides of a portion of said living cell attaching and holding portion where said plurality of living cell accommodation concaves are formed and are extended in said longitudinal direction of said living cell attaching and holding portion.

12. The living cell cryopreservation tool according to claim 10, wherein said liquid nitrogen-resistant synthetic resin is 3-polyethylene fluoride, low-density polyethylene, medium-density polyethylene, high-density polyethylene, polycarbonate, nylon, polysulfone, polyester, polystyrene, polyimide, ultra-high-molecular-weight polyethylene, ethylene-vinyl acetate copolymer or laminates of films formed of the synthetic resin.

13. A living cell cryopreservation tool comprising:
a body part and a living cell holding part projecting from said body part toward the distal side of said living cell holding member;
wherein said body part is formed of a liquid nitrogen-resistant synthetic resin;
said living cell holding part is formed of a liquid nitrogen-resistant synthetic resin;
said living cell holding part is plate-shaped and extends in a longitudinal direction of said living cell cryopreservation tool;
said living cell holding part has a plurality of living cell accommodation concaves provided on a surface of said plate-shaped living cell holding part;
said plurality of living cell accommodation concaves are arranged in said longitudinal direction of said living cell cryopreservation tool;
said living cell accommodation concaves are approximately hemispherical concave portions;
said living cell holding part has a groove communicating with said living cell accommodation concave and said living cell accommodation concave adjacent to each other;
said living cell holding part has a distal groove extended toward a distal end thereof from said living cell accommodation concave positioned to a distal side than any other living cell accommodation concaves;
said living cell holding part has a proximal groove extended toward a proximal end thereof from said living cell accommodation concave positioned to a proximal side than any other living cell accommodation concaves;

said grooves having cryopreservation liquid discharge passages in said living cell accommodation concave; and said living cell holding part has a projected portion formed at a distal end side thereof than said living cell accommodation concave positioned nearer to said distal end thereof than said other living cell accommodation concaves.

14. The cell cryopreservation tool according to claim 13, wherein each of said plurality of living cell accommodation concaves is spaced at regular intervals.

15. The living cell cryopreservation tool according to claim 13, wherein said liquid nitrogen-resistant synthetic resin is 3-polyethylene fluoride, low-density polyethylene, medium-density polyethylene, high-density polyethylene, polycarbonate, nylon, polysulfone, polyester, polystyrene, polyimide, ultra-high-molecular-weight polyethylene, ethylene-vinyl acetate copolymer or laminates of films formed of the synthetic resin.

\* \* \* \* \*